(12) United States Patent
Barron et al.

(10) Patent No.: US 11,510,890 B2
(45) Date of Patent: Nov. 29, 2022

(54) MEROTERPENOID COMPOUNDS FOR USE IN THE PREVENTION AND TREATMENT OF A NEUROLOGICAL DISORDER

(71) Applicant: SOCIETE DES PRODUITS NESTLE S.A., Vevey (CH)

(72) Inventors: Denis Marcel Barron, Lutry (CH); Yann Ratinaud, Morges (CH); Jonathan Thevenet, Publier (FR); Andreas Christian Wiederkehr, Blonay (CH)

(73) Assignee: Societe des Produits Nestle S.A., Vevey (CH)

( * ) Notice: Subject to any disclaimer, the term of this patent is extended or adjusted under 35 U.S.C. 154(b) by 109 days.

(21) Appl. No.: 16/647,229

(22) PCT Filed: Sep. 13, 2018

(86) PCT No.: PCT/EP2018/074805
§ 371 (c)(1),
(2) Date: Mar. 13, 2020

(87) PCT Pub. No.: WO2019/053159
PCT Pub. Date: Mar. 21, 2019

(65) Prior Publication Data
US 2020/0405676 A1    Dec. 31, 2020

(30) Foreign Application Priority Data
Sep. 15, 2017   (EP) .................................... 17191464

(51) Int. Cl.
*A61K 31/216*      (2006.01)
*A61K 31/11*       (2006.01)

(52) U.S. Cl.
CPC ............ *A61K 31/216* (2013.01); *A61K 31/11* (2013.01)

(58) Field of Classification Search
CPC .................................................. A61K 31/216
See application file for complete search history.

(56) References Cited

U.S. PATENT DOCUMENTS

2007/0054966 A1    3/2007   Kitahara et al.

FOREIGN PATENT DOCUMENTS

| CN | 101422450 | | 5/2009 | | |
|---|---|---|---|---|---|
| CN | 102786414 | A | 11/2012 | | |
| EP | 1142870 | | 10/2001 | | |
| EP | 1142870 | A1 * | 10/2001 | ............. | A61K 31/12 |
| EP | 1176134 | | 1/2002 | | |
| JP | S55113712 | A | 9/1980 | | |
| JP | H09165332 | A | 6/1997 | | |
| JP | 2006213644 | | 8/2006 | | |
| JP | 2006213644 | A * | 8/2006 | | |
| WO | 9405274 | | 3/1994 | | |
| WO | 2013059606 | | 4/2013 | | |
| WO | WO-2013059606 | A1 * | 4/2013 | ............. | A61K 31/11 |

OTHER PUBLICATIONS

Shen et al., "Discovery of a new structural class of Competitive hDHODH inhibitors with in vitro and in vivo anti-inflammatory, immunosuppressive effect", European J. of Pharmacology, vol. 791, Sep. 3, 2016, pp. 205-212.*
Maekawa et al. "Basal and stimulated lactate fluxes in primary cultures of astrocytes are differentially controlled by distinct proteins" Journal of Neurochemistry, 2008, vol. 107, pp. 789-798.
Bolanos, Juan P. "Bioenergetics and redox adaptations of astrocytes to neuronal activity" Journal of Neurochemistry, 2016, vol. 139, suppl. 2, pp. 115-125.
Weidner et al. "Amorfrutins are potent antidiabetic dietary natural products" PNAS, May 8, 2012, vol. 109, No. 19, pp. 7257-7262.
Shen et al. "Discovery of a new structural class of competitive hDHODH inhibitors with in vitro and in vivo anti-inflammatory, immunosuppressive effects" European Journal of Pharmacology, 2016, vol. 791, pp. 205-212.
Magistretti et al. "Neuron-glia metabolic coupling: Role in plasticity and neuroprotection" Journal of Neurological Sciences, 2017, vol. 381, p. 24.
Robertson et al., "Synergistic Inhibition of Aβ Production by Combinations of γ-Secretase Modulators", European Journal of Pharmacology, vol. 812, Jul. 8, 2017, pp. 104-112.
China Patent Office Communication for Application No. 201880057034.0, dated Oct. 9, 2022, 10 pages.
Miyamoto et al., "Astrocyte-Neuron Lactate Shuttle Sensitizes Nociceptive Transmission in the Spinal Cord", Glia, vol. 67, 2019, pp. 27-36.
Papadopoulou et al., "Therapeutic Approaches in Locked-in Syndrome", Folia Medica, vol. 61, Issue No. 3, 2018, pp. 343-351.
Izawa et al., "Pioglitazone Enhances Pyruvate and Lactate Oxidation in Cultured Neurons but not in Cultured Astroglia", Brain Research, vol. 1305, 2009, pp. 64-73.
Darby et al., "Whole Cell Screen for Inhibitors of PH Homeostasis in Mycobacterium Tuberculosis", Pios One, vol. 8, Issue No. 7,2013, pp. 1-12.
Zhang et al., "Anti-Inflammatory Sesquiterpenoids from a Sponge-Derived Fungus *Acremonium* sp." Journal of Natural Products, vol. 72, Issue No. 2, 2009, pp. 270-275.

(Continued)

*Primary Examiner* — Svetlana M Ivanova
(74) *Attorney, Agent, or Firm* — K&L Gates LLP

(57) ABSTRACT

The present invention relates to a compound, in particular a meroterpenoid compound, or salt thereof, for use in the prevention and/or treatment of a neurological disorder in an individual. The compound of the invention can promote lactate secretion. A composition comprising the compound of the invention, and a food or food extract enriched with said compound or composition is also provided.

9 Claims, 5 Drawing Sheets

(56) References Cited

OTHER PUBLICATIONS

Isaka et al., "Ascochlorin Derivatives from the Leafhopper Pathogenic Fungus *Microcera* Sp. BCC 17074", The Journal of Antibiotics, vol. 68, 2015, pp. 47-51.
Kawaguchi et al., "A New Ascochlorin Derivative from Cylindrocarpon Sp. FKI-4602", The Journal of Antibiotics, vol. 66, 2013, pp. 23-29.
Japan Patent Office Communication for Application No. 2020-508497, Dispatch No. 432892, Dispatch Date Sep. 6, 2021, 9 pages.

* cited by examiner

A

B

C

D

E

F

G

H

I

J

A (CAS 26166-39-2)

B (CAS 22738-98-3)

C (CAS 22562-67-0)

D (CAS 38965-84-3)

E (CAS 22581-11-9)

F (CAS 22562-68-1)

G (CAS 165187-16-6)

H (CAS 25999-31-9)

I (CAS 80489-90-3)

MEROTERPENOID COMPOUNDS FOR USE IN THE PREVENTION AND TREATMENT OF A NEUROLOGICAL DISORDER

CROSS REFERENCE TO RELATED APPLICATIONS

The present application is a National Stage of International Application No. PCT/EP2018/074805, filed on Sep. 13, 2018, which claims priority to European Patent Application No. 17191464.1, filed on Sep. 15, 2017, the entire contents of which are being incorporated herein by reference.

INTRODUCTION

The brain is a energy demanding organ as many processes linked to neurons and glial cells require a lot of energy in the form of ATP. In neurons, electrical activity, the restoration of ion gradients across the plasma membrane as well as synaptic transmission are examples of biological processes that require high levels of energy supply. The brain is therefore strongly dependent on the continuous provision of glucose as neurons do not store glycogen and are unable to oxidize fats as an alternative fuel source.

Glucose metabolism is initiated in the glycolytic pathway that forms ATP, NADH and either of two end-products pyruvate or lactate. In a second step, pyruvate oxidized in the mitochondrial matrix is required to initiate the synthesis of the large majority of ATP molecules to maintain neuronal energy homeostasis. The ability of cells of the central nervous system to generate sufficient amounts of energy is essential for brain function. In the aging brain, glucose metabolism is reduced, which may explain declining cognitive function as we get older. Glucose hypometabolism has also been observed in individuals at risk of developing Alzheimer's disease long before clinical symptoms are detected. Interventions improving brain energy metabolism may therefore be used to prevent cognitive decline during normal aging or neurological diseases.

In addition to glucose, neurons are able to oxidize other fuels such as amino acids (mainly glutamate and glutamine), ketone bodies, lactate and pyruvate. During fasting for instance, ketone bodies serve as an important fuel source gradually replacing glucose during the transition from fasting to starvation. Lactate is a particularly important mitochondrial substrate. It is dehydrogenated to pyruvate, which can then be fully oxidized by mitochondria to form $CO_2$. Oxidative metabolism of pyruvate is coupled to mitochondrial electron transport and respiration resulting in ATP synthesis. In the central nervous system, lactate also has a signaling function, stimulating for example hypoxia-induced factor 1a and down-stream signaling causing transcriptional changes in brain cells.

The source of lactate can be several fold. When neurons are electrically active, they accelerate their glycolytic pathway to the extent that mitochondria are no longer able to keep up with pyruvate oxidation. Instead, pyruvate is transiently converted to lactate in a process which has been termed aerobic glycolysis. In this situation, the accumulating lactate may exert its signaling role in neurons stabilizing for example hypoxia-induced factor 1α or inducing the expression of brain-derived neurotrophic factor, which is important for neuronal survival and long-term memory. A second and even more important source of lactate are astrocytes. This cell type is metabolically closely linked both to neurons and cerebral blood vessel capillaries.

A main function of astrocytes is to sense synaptic activity and regulate the uptake as well as transfer of nutrients from the blood stream to neurons. Astrocytes are highly glycolytic. Their metabolism of glucose therefore mainly ends in the formation of lactate with only a fraction of pyruvate entering mitochondria for oxidation. Lactate synthesized by astrocytes is exported and taken up by neighboring neurons via monocarboxylate transporters. Here lactate serves as a fuel for neuronal mitochondria. This metabolic connection has been termed the astrocyte neuron lactate shuttle (ANLS).

A third source of lactate for the brain is the direct uptake from the periphery. During exercise systemic blood concentrations of lactate increase and cross the blood brain barrier to be metabolized by neurons. In this way, peripherally generated lactate contributes to brain energy metabolism. Exercise has been shown to improve memory function. Lactate may be an important metabolite explaining this effect of exercise on learning.

The importance of lactate on learning has been convincingly demonstrated when studying the ANLS. Lowering the expression of specific monocarboxylate transporters impairs the transfer of lactate from astrocytes to neurons and thereby long-term memory formation.

Modulation of lactate levels in the brain therefore has the potential to improve cognitive function. At the same time lactate either as a signaling molecule or as a fuel for mitochondria may influence neurological diseases where chronic or acute energy deficits need to be corrected.

Alzheimer's disease (AD) is the most common cause of dementia. Currently, there is no cure for AD. Only symptomatic treatments exist, and these exert their beneficial effects mainly by restoring lowered neurotransmitter levels. Hypometabolism of glucose is a metabolic alteration likely occurring early during AD progression. Correction of brain metabolism is a promising approach to delay disease progression. Restoration of brain energy homeostasis has also been tested to restore mild cognitive impairment in the elderly.

Epilepsy is the fourth most common neurological disorder. Up to 30% of children with epilepsy continue to have seizures despite anticonvulsant treatment. Ketogenic diets successfully lower the frequency of seizures in children with intractable epilepsy. However, these diets are very high in fat and therefore highly unpalatable.

In epilepsy, local excessive electrical activity may result in the inability of neurons to cope with their energy load and the rapid provision of mitochondrial fuel may be beneficial. Transient formation of peripheral lactate or enhanced provision through the ANLS could be protective for neurons during recovery from a seizure.

Stroke is the most common cause of handicap and the third most common cause of death in adults worldwide. Tissue plasminogen activator (tPA) is the only Federal Drug Administration-approved treatment for ischemic stroke. The drawback of this treatment is that it can be effective only when administered during short time windows (within 3 hours) after ischemia. Endovascular procedure can be used to remove the clot blocking the artery but only after tPA treatment and within 6 hours of the ischemia. Strict criteria determine the eligibility of a patient for this procedure. Considering that only very limited treatment options exist, there is a need for new stroke treatments.

Targeting brain metabolism may prove useful in stroke to rapidly restore energy supply as neurons are transiently deprived of oxygen and nutrients. In a preclinical model of stroke (transient middle cerebral artery occlusion), lactate has been successfully tested for its ability to prevent neuronal loss.

Taken together, modulating metabolism to enhance the availability of lactate for neurons may have beneficial effects in mild cognitive impairment during aging or neurological diseases with suspected energy deficits in neurons.

The inventors of the present application have identified meroterpenoids (particularly ascochlorin and related compounds) as bioactives that promote lactate secretion from astrocytes. These active compounds affect the astrocyte neuron lactate shuttle or stimulate lactate release from other tissues and may thereby be beneficial for brain energy homeostasis and neuronal health by counteracting the negative effects of impaired metabolism.

DETAILED DESCRIPTION

Definitions

As used in this disclosure and the appended claims, the singular forms "a," "an" and "the" include plural referents unless the context clearly dictates otherwise. Thus, for example, reference to "a component" or "the component" includes two or more components.

The term "analogue" as used herein is understood to refer to a compound having a structure similar to that of another one, but differing from it in respect of a certain component. A "derivative" is a compound that can be imagined to arise or actually be synthesized from a parent compound by replacement of one atom with another atom or group of atoms.

All percentages expressed herein are by weight of the total weight of the composition unless expressed otherwise. As used herein, "about," "approximately" and "substantially" are understood to refer to numbers in a range of numerals, for example the range of −10% to +10% of the referenced number, preferably −5% to +5% of the referenced number, more preferably −1% to +1% of the referenced number, most preferably −0.1% to +0.1% of the referenced number. All numerical ranges herein should be understood to include all integers, whole or fractions, within the range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

The components of the chemical structures described herein can be defined as follows: as used herein, the term "Halogen" can be a fluorine, chlorine, a bromine or an iodine atom. As used herein "Isoprenoid chain", the building blocks of which are five carbon branched-chain unsaturated hydrocarbons biosynthetically derived from dimethylallyl pyrophosphate and its isomer isopentenyl pyrophosphate. Unsaturated means it contains at least one double bond between carbon atoms. Isoprenoid chains may contain one or more of these unsaturated five carbon units. Isoprenoid chains may for example but not exclusively comprise 3,3-dimethyllalyl, 1,1-dimethylallyl, geranyl, linalyl, farnesyl, nerolidyl, and geranylgeranyl chains. "Modified isoprenoid" chain means that the original isoprenoid backbone has been further modified, biosynthetically and/or chemically. Such modifications may for example but not exclusively include reduction of double bonds, stepwise carbon oxidation to hydroxyl, aldehyde, and carboxylic acid groups, carbon loss, rearrangement of carbon atoms, rearrangement of double bonds, esterification of hydroxyls, amidation of carboxyls, cyclization. "Cyclized chain" is related to a chain having atoms arranged in a ring or closed-chain structure. "Hydroxylated" means a structure modified by hydroxylation, i.e. the introduction of a hydroxyl group. "Open chain" is a chain with a linear structure, i.e. having no ring in its structure. A "modified phenethyl chain" means that the original phenethyl backbone has been further modified, biosynthetically and/or chemically. Such modifications may for example but not exclusively include reduction of the double bond.

The words "comprise," "comprises" and "comprising" are to be interpreted inclusively rather than exclusively. Likewise, the terms "include," "including" and "or" should all be construed to be inclusive, unless such a construction is clearly prohibited from the context. Nevertheless, the compositions disclosed herein may lack any element that is not specifically disclosed herein. Thus, a disclosure of an embodiment using the term "comprising" includes a disclosure of embodiments "consisting essentially of" and "consisting of" the components identified. A composition "consisting essentially of" contains at least 50 wt. % of the referenced components, preferably at least 75 wt. % of the referenced components, more preferably at least 85 wt. % of the referenced components, most preferably at least 95 wt. % of the referenced components.

The term "and/or" used in the context of "X and/or Y" should be interpreted as "X," or "Y," or "X and Y." Where used herein, the terms "example" and "such as," particularly when followed by a listing of terms, are merely exemplary and illustrative and should not be deemed to be exclusive or comprehensive.

The terms "food," "food product" and "food composition" mean a product or composition that is intended for ingestion by an individual such as a human and provides at least one nutrient to the individual. The compositions of the present disclosure, including the many embodiments described herein, can comprise, consist of, or consist essentially of the elements disclosed herein, as well as any additional or optional ingredients, components, or elements described herein or otherwise useful in a diet.

Cognitive function is responsible for brain functions including the processing of information, memory capacities, situation dependent judgment, learning ability and memory.

The terms "impaired memory function during aging" and "cognitive impairment during aging" as used herein means a reduction of cognitive function or impairment of any subcategory linked to brain function compared to the control healthy individual when using cognitive testing. Such cognitive testing usually includes measures of memory, language, ability to orient and attention span.

The term "meroterpenoid" refers to a class of natural products of mixed biosynthetic origin which are partially derived from terpenoids.

The term "neurological disorder" as used herein means any disorder of the nervous system. Such disorders can be the result of disease and accelerated loss of brain function during aging but could also be due to genetic variations or caused by malnutrition.

"Prevention" includes reduction of risk and/or severity of a condition or disorder. The terms "treatment," "treat," "attenuate" and "alleviate" include both prophylactic or preventive treatment (that prevent and/or slow the development of a targeted pathologic condition or disorder) and curative, therapeutic or disease-modifying treatment, including therapeutic measures that cure, slow down, lessen symptoms of, and/or halt progression of a diagnosed pathologic condition or disorder, and include treatment of patients at risk of contracting a disease or suspected to have contracted a disease, as well as patients who are ill or have been diagnosed as suffering from a disease or medical condition. The term does not necessarily imply that an individual is treated until total recovery. These terms also refer to the maintenance and/or promotion of health in an individual not suffering from a disease but who may be susceptible to the development of an unhealthy condition. These terms are also intended to include the potentiation or otherwise enhancement of one or more primary prophylactic or therapeutic measure. The terms "treatment," "treat," "attenuate" and "alleviate" are further intended to include the dietary management of a disease or condition or the dietary management for prophylaxis or prevention a disease or condition. A treatment can be patient- or doctor-related.

The term "individual" means any animal, including humans, that could suffer from a neurological disorder and thus benefit from one or more of the methods disclosed herein. Generally, the individual is a human or an avian, bovine, canine, equine, feline, hicrine, lupine, murine, ovine or porcine animal. A "companion animal" is any domesticated animal, and includes, without limitation, cats, dogs, rabbits, guinea pigs, ferrets, hamsters, mice, gerbils, horses, cows, goats, sheep, donkeys, pigs, and the like. Preferably, the individual is a human or a companion animal such as a dog or cat. The compound of the invention can be used for the prevention or treatment of disorders relating to brain health, particularly neurological disorders.

A human individual who is elderly may benefit. An individual is considered as "elderly" if it has surpassed the first half of its average expected lifespan in its country of origin, preferably, if it has surpassed the first two thirds of the average expected lifespan in its country of origin, more preferably if it has surpassed the first three quarters of the average expected lifespan in its country of origin, most preferred if it has surpassed the first four fifths of the average expected lifespan in its country of origin. A human individual who is an infant under 5 years of age, may also benefit.

As used herein, an "effective amount" is an amount that prevents a deficiency, treats a disease or medical condition in an individual or, more generally, reduces symptoms, manages progression of the diseases or provides a nutritional, physiological, or medical benefit to the individual. The relative terms "improved," "increased," "enhanced" and the like refer to the effects of the composition disclosed herein relative to a composition lacking one or more ingredients and/or having a different amount of one or more ingredients, but otherwise identical.

Compound of the Invention

The present invention relates to a compound of structural formula (Ia)

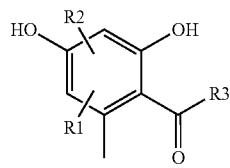

wherein R1=H or a halogen;
R2=an isoprenoid chain or a modified isoprenoid chain comprising 1 to 19 carbon atoms, hydrogen, and optionally oxygen; and
R3=H or OH.
or a salt thereof for use in the prevention and/or treatment of a neurological disorder in an individual.

In some embodiments, R1=H or a halogen; R2=an isoprenoid chain comprising 1 to 19 carbon atoms, hydrogen, and optionally oxygen; and R3=H or OH.

In some embodiments, R1=H or a halogen; R2=an isoprenoid chain comprising 1 to 10 carbon atoms, hydrogen, and optionally oxygen; and R3=H or OH.

In some embodiments, R1=H or a halogen; R2=an isoprenoid chain comprising 1 to 5 carbon atoms, hydrogen, and optionally oxygen; and R3=H or OH.

In some embodiments, R1=a halogen; R2=an isoprenoid chain comprising 1 to 19 carbon atoms, hydrogen, and optionally oxygen; and R3=H or OH.

In some embodiments, R1=a halogen; R2=an isoprenoid chain comprising 1 to 19 carbon atoms, hydrogen, and oxygen; and R3=H or OH.

In some embodiments, R1=halogen; R2=an isoprenoid chain comprising 1 to 10 carbon atoms, hydrogen, and oxygen; and R3=H or OH.

In some embodiments, R1=halogen; R2=an isoprenoid chain comprising 1 to 5 carbon atoms, hydrogen, and oxygen; and R3=H or OH.

In some embodiments, R1=Cl; R2=an isoprenoid chain comprising 1 to 5 carbon atoms, hydrogen, and oxygen; and R3=H.

In one embodiment, compounds of structural formula (Ia) can be represented as follows:

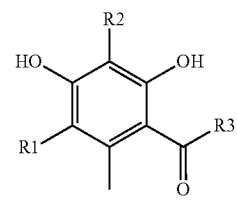

In one embodiment, the compound is for use in the prevention and/or treatment of a neurological disorder in an individual wherein lactate secretion is promoted.

In one embodiment, the compound is for use in the prevention and/or treatment of a neurological disorder in an individual wherein lactate secretion from astrocytes is promoted.

In one embodiment, the compound is for use in the prevention and/or treatment of a neurological disorder in an individual wherein lactate secretion is promoted from peripheral tissues.

In one embodiment, the compound is for use in the prevention of cognitive decline in an individual wherein lactate secretion is promoted.

In one embodiment, the individual is a human, in particular an elderly human individual or an infant human individual. In one embodiment, the individual is a companion animal.

In one embodiment, the compound is a meroterpenoid. In one embodiment, the compound can be found in nature.

In one embodiment, the compound is an isoprenoid phenol. In one embodiment, the compound is a prenyl phenol. In one embodiment, the compound is a terpenoid derivative.

In one embodiment, the compound has structural formula (Ib).

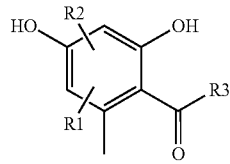

wherein R1=H or a halogen;
R2=a cyclized isoprenoid chain or a modified cyclized isoprenoid chain comprising 1 to 19 carbon atoms, hydrogen, and optionally oxygen; and
R3=H or OH.

In some embodiments, R1=H or a halogen; R2=a cyclized isoprenoid chain comprising 1 to 19 carbon atoms, hydrogen, and optionally oxygen; and R3=H or OH.

In some embodiments, R1=H or a halogen; R2=a cyclized isoprenoid chain comprising 1 to 10 carbon atoms, hydrogen, and optionally oxygen; and R3=H or OH.

In some embodiments, R1=H or a halogen; R2=a cyclized isoprenoid chain comprising 1 to 5 carbon atoms, hydrogen, and optionally oxygen; and R3=H or OH.

In some embodiments, R1=a halogen; R2=a cyclized isoprenoid chain comprising 1 to 19 carbon atoms, hydrogen, and oxygen; and R3=H or OH.

In some embodiments, R1=a halogen; R2=a cyclized isoprenoid chain comprising 1 to 10 carbon atoms, hydrogen, and oxygen; and R3=H or OH.

In some embodiments, R1=a halogen; R2=a cyclized isoprenoid chain comprising 1 to 5 carbon atoms, hydrogen, and oxygen; and R3=H or OH.

In some embodiments, R1=Cl; R2=a cyclized isoprenoid chain comprising 1 to 19 carbon atoms, hydrogen, and oxygen; and R3=H.

In some embodiments, R1=Cl; R2=a cyclized isoprenoid chain comprising 1 to 10 carbon atoms, hydrogen, and oxygen; and R3=H.

In some embodiments, R1=Cl; R2=a cyclized isoprenoid chain comprising 1 to 5 carbon atoms, hydrogen, and oxygen; and R3=H.

In one embodiment, compounds of structural formula (Ib) can be represented as follows:

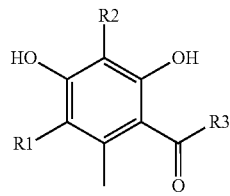

In one embodiment, R1=Cl.
In one embodiment, R3=H.
In one embodiment, R1=Cl and R3=H.
In one embodiment, R1=Cl; R2=a cyclized isoprenoid chain comprising 1 to 19 carbon atoms, hydrogen, and optionally oxygen; and R3=H.

In some embodiments, R1=Cl; R2=a cyclized isoprenoid chain comprising 1 to 10 carbon atoms, hydrogen, and optionally oxygen; and R3=H.

In some embodiments, R1=H or a halogen; R2=a cyclized isoprenoid chain comprising 1 to 5 carbon atoms, hydrogen, and optionally oxygen; and R3=H or OH.

In some embodiments, R1=Cl; R2=a cyclized isoprenoid chain comprising 1 to 19 carbon atoms, hydrogen, and oxygen; and R3=H.

In some embodiments, R1=Cl; R2=a cyclized isoprenoid chain comprising 1 to 10 carbon atoms, hydrogen, and oxygen; and R3=H.

In some embodiments, R1=Cl; R2=a cyclized isoprenoid chain comprising 1 to 5 carbon atoms, hydrogen, and oxygen; and R3=H.

For example, the compound may be selected from the list comprising CAS 26166-39-2 (Ascochlorin or Ilicicolin D); CAS 22562-68-1 (Antibiotic LL-Z 1272ε); CAS 165187-16-6 (Cylindrol B); CAS 22562-67-0 (Ilicicolin C); CAS 23887-67-4 (Ilicicolin E); CAS 22738-98-3 (Ilicicolin F); CAS 80557-12-6 (Grifolic acid); and CAS 22851-11-9.

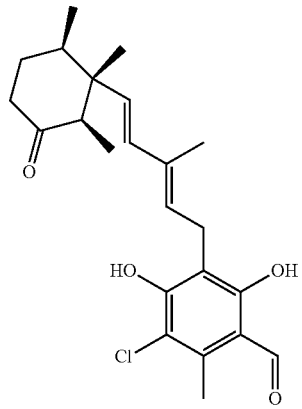

CAS 26166-39-2
Ascochlorin =
Ilicicolin D

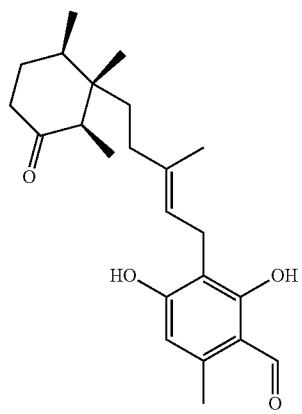

CAS 22562-68-1
Antibiotic LL-Z 1272ε

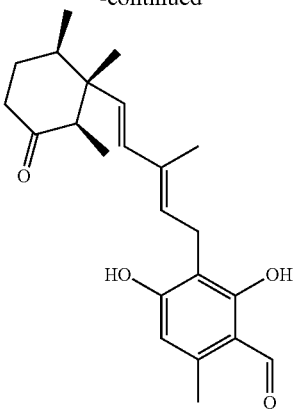

CAS 165187-16-6
Cylindrol B

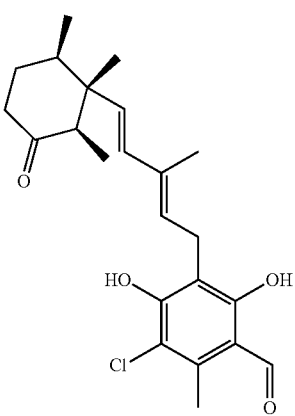

CAS 22562-67-0
Ilicicolin C

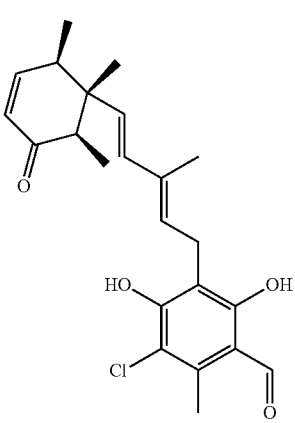

CAS 23887-67-4
Ilicicolin E

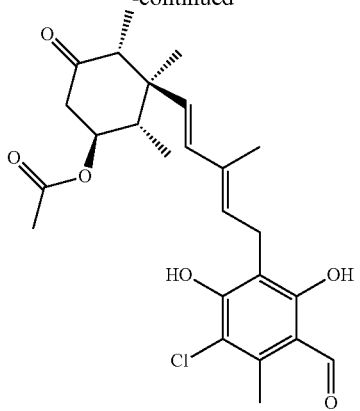

CAS 22738-98-3
Ilicicolin F

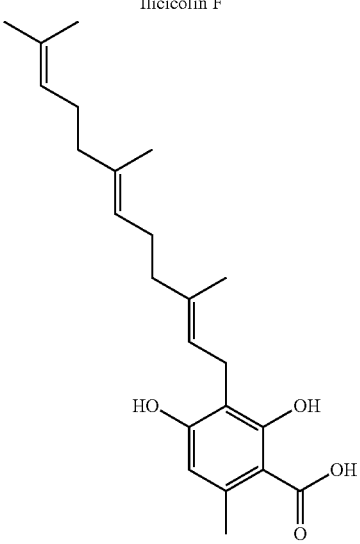

CAS 80557-12-6
Grifolic Acid

In a preferred embodiment, the compound is CAS 26166-39-2 (Ascochlorin or Illicicolin D), or an analogue or derivative thereof.

In a preferred embodiment, the compound is CAS 22562-67-0 (Illicicolin C), or an analogue or derivative thereof.

In a preferred embodiment, the compound is CAS 22738-98-3 (Illicicolin F), or an analogue or derivative thereof.

Ascochlorin and derivatives thereof can be found in or produced by fungal species, for example *Acremonium* sp., *Acremoninum luculae*, *Ascochyta oiciae*, *Asochyta viciae*, *Cephalosporium diospyri*, *Cylindrocarpon lucidum*, *Fusarium* sp., *Nectria galligena*, *Nectria coccinea*, *Nigrosabulum globosum*, *Verticillium* sp.

In some embodiments, said compound has structural formula (Ic).

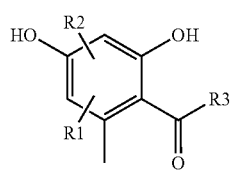

wherein R1=H or a halogen;
R2=a cyclized isoprenoid chain with further hydroxylated side chain structure or a modified cyclized isoprenoid chain structure with further hydroxylated side chain structure and optionally further esterification comprising 1 to 19 carbon atoms, hydrogen, and optionally oxygen; and
R3=H or OH.

In one embodiment, compounds of structural formula (Ic) can be represented as follows:

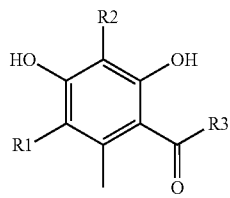

In one embodiment, R1=Cl.

In one embodiment, R3=H.

In one embodiment, R2=a cyclized isoprenoid chain with further hydroxylated side chain structure and optionally further esterification comprising 1 to 19 carbon atoms, hydrogen, and optionally oxygen.

In one embodiment, R1=Cl; R3=H; and R2=a cyclized isoprenoid chain with further hydroxylated side chain structure and further esterification comprising 1 to 19 carbon atoms, hydrogen, and oxygen.

In one embodiment, R1=Cl; R3=H; and R2=a cyclized isoprenoid chain with further hydroxylated side chain structure and further esterification comprising 1 to 10 carbon atoms, hydrogen, and oxygen.

In one embodiment, R1=Cl; R3=H; and R2=a cyclized isoprenoid chain with further hydroxylated side chain structure and further esterification comprising 1 to 5 carbon atoms, hydrogen, and oxygen.

For example, said compound may be selected from the list comprising CAS 38561-36-3 (Deacetylchloronectrin); CAS 53730-27-1 (Hydroxyhydroascochlorin); CAS 38965-84-3 (Chloronectrin); CAS 1654004-69-9 (Nectchlorin A); CAS 165187-17-7 (Cylindrol A4); and CAS 1651819-33-8.

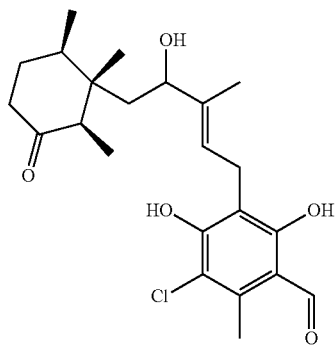

CAS 38561-36-3
Deacetylchloronectrin

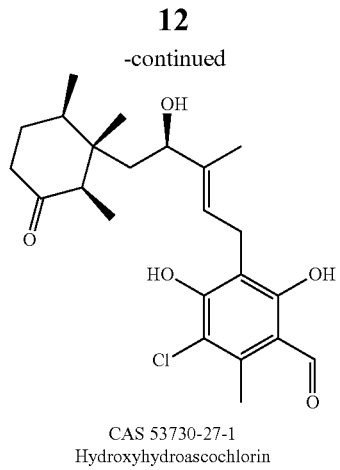

CAS 53730-27-1
Hydroxyhydroascochlorin

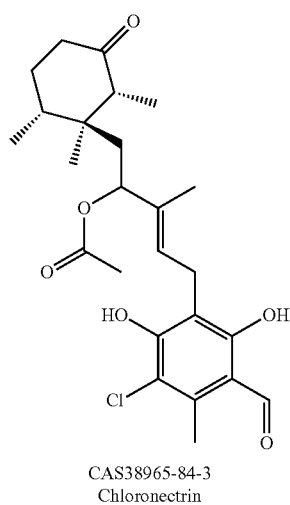

CAS 38965-84-3
Chloronectrin

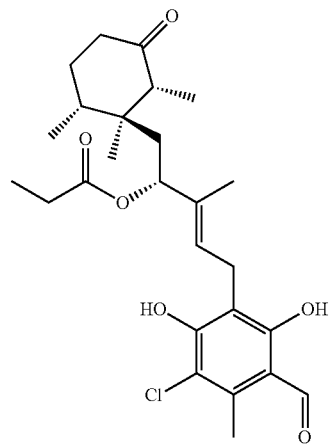

CAS 1654004-69-9
Nectchlorin A

-continued

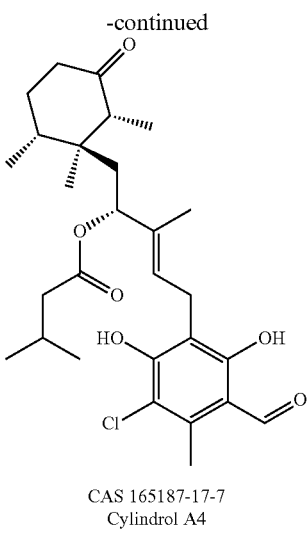

CAS 165187-17-7
Cylindrol A4

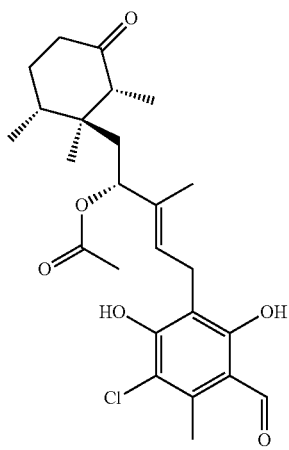

CAS 1651819-33-8

In a preferred embodiment, the compound is CAS 38965-84-3 (Chloronectrin) or an analogue or derivative thereof.

In some embodiments, said compound has structural formula (Id).

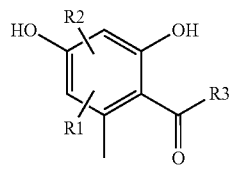

wherein R1=H or a halogen;
R2=an open isoprenoid chain or a modified open isoprenoid chain comprising 1 to 19 carbon atoms, hydrogen, and optionally oxygen; and
R3=H or OH.

In one embodiment, compounds of structural formula (Id) can be represented as follows:

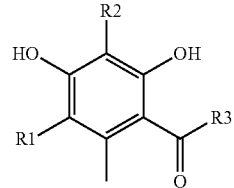

For example, said compound may be selected from the list comprising CAS 83324-56-5 (Colletorin B); CAS 83324-48-5 (Colletochlorin B); CAS 22581-07-3 (Illicicolin B), CAS 22581-06-2 (Illicicolin A), CAS 1114927-87-5 (Chlorocylindrocarpol), and CAS1654004-70-2 (Nectchlorin B).

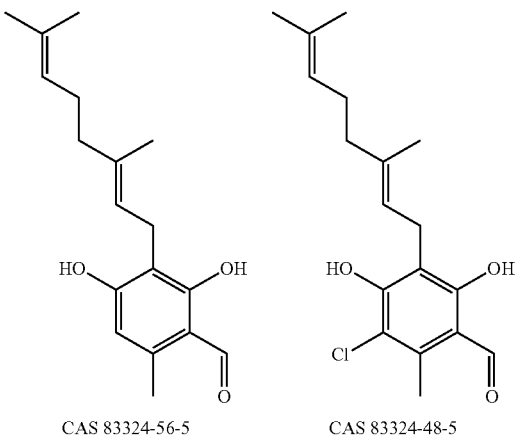

CAS 83324-56-5
Colletorin B

CAS 83324-48-5
Colletochlorin B

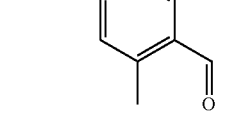

CAS 22581-07-3
Ilicicolin B

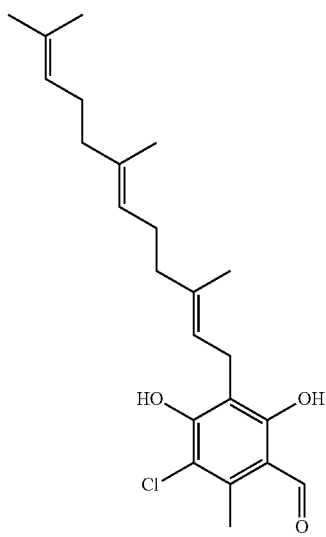

CAS 22581-06-2
Ilicicolin A

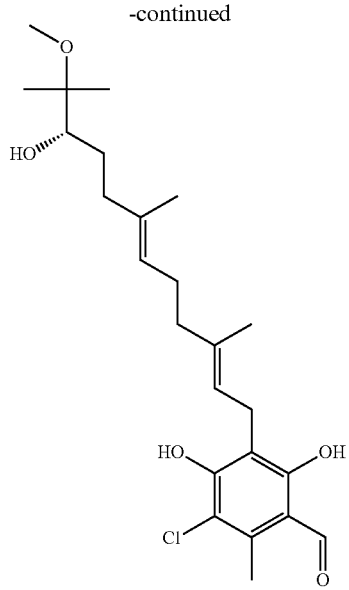

CAS 1654004-70-2
Nectchlorin B

The present invention also relates to a compound having a structural formula (II).

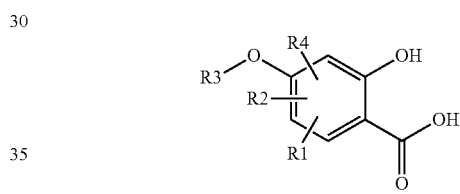

wherein R1=phenethyl or a modified phenethyl side chain, and/or an isoprenoid chain or a modified open isoprenoid chain comprising 1 to 19 carbon atoms, hydrogen, and optionally oxygen;
R2=H or an isoprenoid chain or a modified open isoprenoid chain comprising 1 to 19 carbon atoms, hydrogen, and optionally oxygen;
R3=H or methyl; and
R4=an isoprenoid chain or a modified open isoprenoid chain comprising 1 to 19 carbon atoms, hydrogen, and optionally oxygen.
or a salt thereof for use in the prevention and/or treatment of a neurological disorder in an individual.

In one embodiment, compounds of structural formula (II) can be represented as follows:

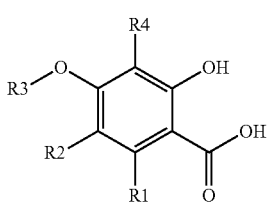

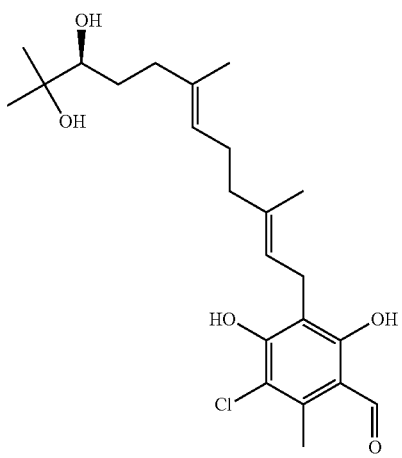

CAS 1114927-87-5
Chlorocylindrocarpol

In one embodiment, the compound of structural formula (II) is for use in the prevention or treatment of a neurological disorder in an individual wherein lactate secretion is promoted.

In one embodiment, the compound is for use in the prevention or treatment of a neurological disorder in an individual wherein lactate secretion from astrocytes is promoted.

In one embodiment, the compound is for use in the prevention or treatment of a neurological disorder in an individual wherein lactate secretion is promoted in peripheral locations.

In one embodiment, the compound is for use in the prevention of cognitive decline in an individual wherein lactate secretion is promoted.

For example, said compound may be selected from the list comprising CAS 80489-90-3 (Amorfrutin); CAS 78916-41-3 (Amorfrutin A); CAS 78916-42-4 (Amorfrutin B=Amorfrutin B1); CAS 73436-04-1 (6-(2-phenylethyl)benzoic acid; 4-O-Demethylamorfrutin B); CAS 1189096-45-4 (Amorfrutin C); CAS 2077965-93-4 (Amorfrutin D); CAS 2074687-78-6 (4-O-Demethylamorfrutin D); and CAS 73436-07-4

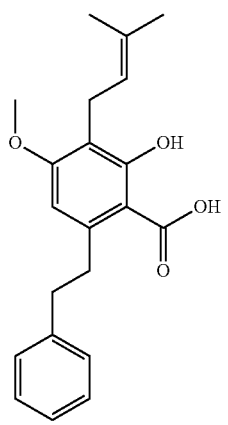

CAS 80489-90-3
Amorfrutin

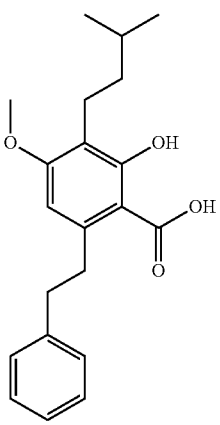

CAS 78916-41-3
Amorfrutin A

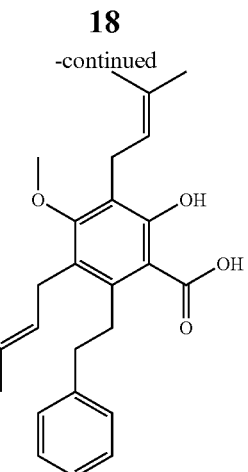

CAS 1189096-45-4
Amorfrutin C

-continued

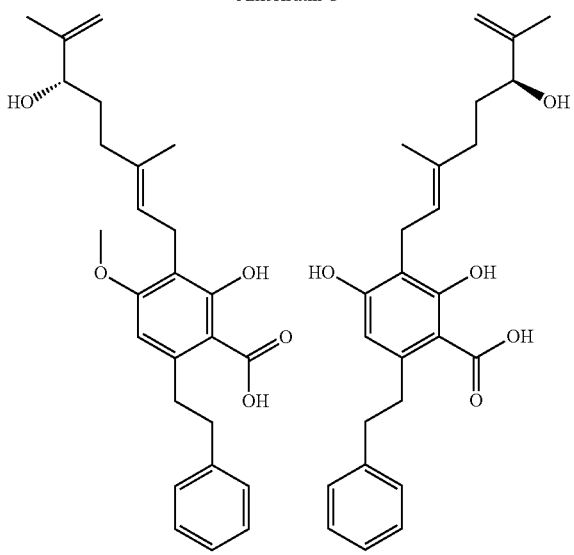

CAS 2077965-93-4
Amorfrutin D

CAS 2074687-78-6
4-O-Demethylamorfrutin D

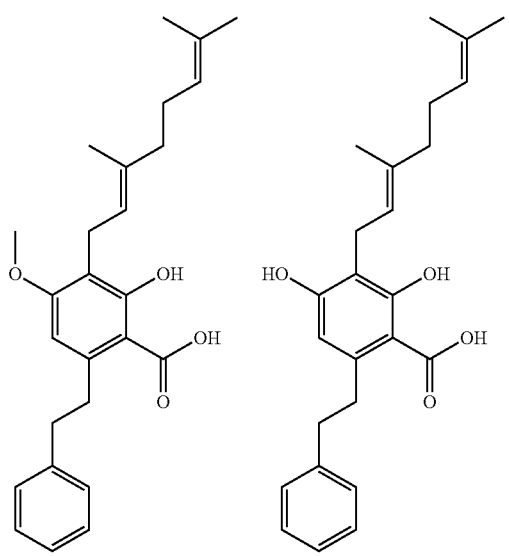

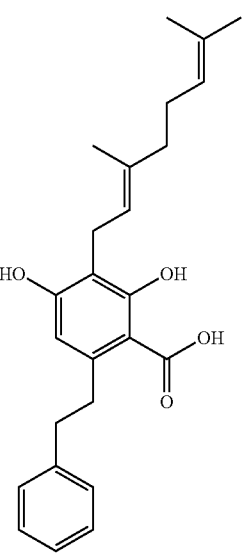

CAS 78916-42-4
Amorfrutin B =
Amorfrutin B1

CAS 73436-04-1
6-(2-phenylethyl)benzoic acid
4-O-Demethylamorfrutin B

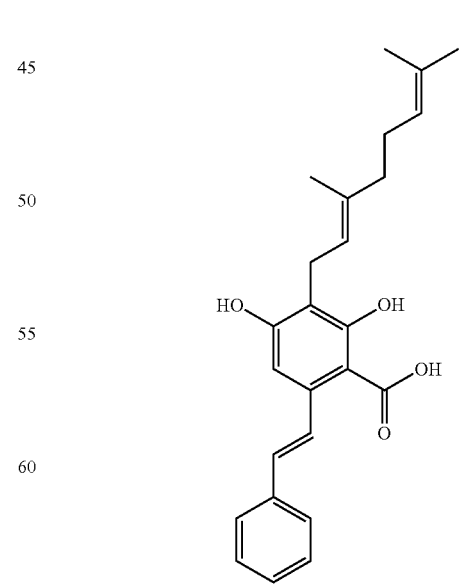

CAS 73436-07-4

In a preferred embodiment, the compound is CAS 80489-90-3 (Amorfrutin) or CAS 73436-04-1 (6-(2-phenylethyl) benzoic acid=4-O-Demethylamorfrutin B).

Amorfrutins may be obtained, for example, from the fruits of *Amorpha fruticosa* or the roots of *Glycyrrhiza foetida*.

The present invention also relates to a compound having a structural formula (III).

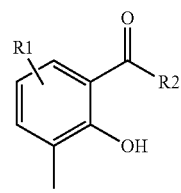

wherein R1=an isoprenoid chain or a modified open isoprenoid chain comprising 1 to 19 carbon atoms, hydrogen, and optionally oxygen
R2=H or OH
or a salt thereof for use in the prevention and/or treatment of a neurological disorder in an individual.

In one embodiment, compounds of structural formula (III) can be represented as follows:

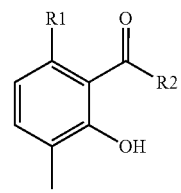

In one embodiment, the compound of structural formula (III) is for use in the prevention or treatment of a neurological disorder in an individual wherein lactate secretion is promoted.

In one embodiment, the compound is for use in the prevention or treatment of a neurological disorder in an individual wherein lactate secretion from astrocytes is promoted.

In one embodiment, the compound is for use in the prevention or treatment of a neurological disorder in an individual wherein lactate secretion is promoted in peripheral locations.

In one embodiment, the compound is for use in the prevention of cognitive decline in an individual wherein lactate secretion is promoted.

For example, said compound may be CAS 25999-31-9 (Lasalocid)

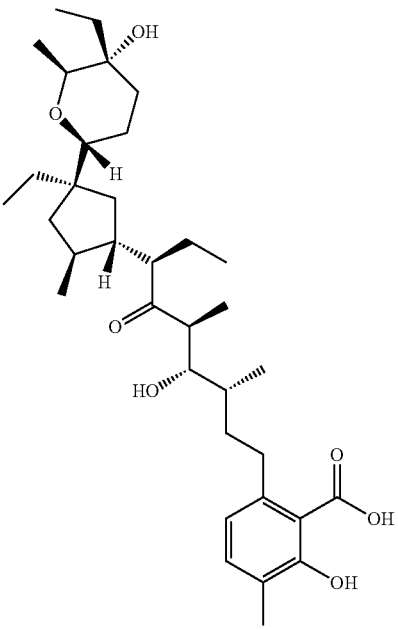

CAS 25999-31-9
Lasalocid

There is also provided a composition comprising an effective amount of the compound of the invention, for use in the prevention or treatment of a neurological disorder in an individual.

In one embodiment, the compound is CAS 26166-39-2 (Ascochlorin or Illicicolin D). In one embodiment, the compound is CAS 22562-67-0 (Illicicolin C). In one embodiment, the compound is CAS 22738-98-3 (Illicicolin F). In one embodiment, the compound is CAS 38965-84-3 (Chloronectrin).

In one embodiment, said composition is a pharmaceutical or nutraceutical composition.

The terms "nutraceutical" combines the words "nutrition" and "pharmaceutical". It is a food or food product that provides health and medical benefits, including the prevention and treatment of disease. A nutraceutical is a product isolated or purified from foods that is generally sold in medicinal forms not usually associated with food. A nutraceutical is demonstrated to have a physiological benefit or provide protection against chronic disease. Such products may range from isolated nutrients, dietary supplements and specific diets to genetically engineered foods, herbal products, and processed foods such as cereals, soups, and beverages.

The term "nutraceutical" as used herein denotes usefulness in both nutritional and pharmaceutical fields of application. Thus, novel nutraceutical compositions can be used as supplements to food and beverages and as pharmaceutical formulations for enteral or parenteral application which may be solid formulations, such as capsules or tablets, or liquid formulations, such as solutions or suspensions.

There is also provided a food or food extract enriched with a compound or composition of the invention. In one embodiment, the compound is selected from Table 2. In one embodiment, the compound is CAS 26166-39-2 (Ascochlorin or Illicicolin D). In one embodiment, the compound is CAS 22562-67-0 (Illicicolin C). In one embodiment, the compound is CAS 22738-98-3 (Illicicolin F), In one embodiment, the compound is CAS 38965-84-3 (Chloronectrin).

Compound for Use in the Prevention or Treatment of Neurological and Other Disorders The compound of the invention can be used for the promotion of lactate secretion in an individual. In one embodiment, the compound is selected from Table 2. In one embodiment, the compound is CAS 26166-39-2 (Ascochlorin or Illicicolin D). In one embodiment, the compound is CAS 22562-67-0 (Illicicolin C). In one embodiment, the compound is CAS 22738-98-3 (Illicicolin F), In one embodiment, the compound is CAS 38965-84-3 (Chloronectrin).

In particular, the compound of the invention can be used for the prevention or treatment of a neurological disorder, for memory dysfunction or for mild cognitive impairment in an individual.

In one embodiment, the compound is selected from Table 2. In one embodiment, the compound is CAS 26166-39-2 (Ascochlorin or Illicicolin D). In one embodiment, the compound is CAS 22562-67-0 (Illicicolin C). In one embodiment, the compound is CAS 22738-98-3 (Illicicolin F), In one embodiment, the compound is CAS 38965-84-3 (Chloronectrin).

In one embodiment, the compound of the invention is used for the prevention or treatment of a neurological disorder. Examples of a neurological disorder include disorders of the central nervous system such as addiction; arachnoid cysts; attention deficit/hyperactivity disorder (ADHD); Autism; Bipolar disorder; Catalepsy; Depression; Encephalitis; Epilepsy/Seizures; Infection; Locked-in syndrome; Meningitis; Migraine; Multiple sclerosis; Myelopathy. Neurological disorders may also include neurodegenerative disorders such as Alzheimer's disease, Huntington's disease, Parkinson's disease, and Tourette's syndrome.

The neurological disorder may be selected from addiction; arachnoid cysts; attention deficit/hyperactivity disorder (ADHD); Autism; Bipolar disorder; Catalepsy; Depression; Encephalitis; Epilepsy/Seizures; Infection; Locked-in syndrome; Meningitis; Migraine; Myelopathy. Neurological disorders may also include neurodegenerative disorders such as Alzheimer's disease, Huntington's disease, Parkinson's disease, and Tourette's syndrome.

The neurological disorder may be selected from attention deficit/hyperactivity disorder (ADHD); Autism; Bipolar disorder; Catalepsy; Infection; Locked-in syndrome; Meningitis; Migraine; Myelopathy.

The neurological disorder may be selected from Alzheimer's disease, Huntington's disease, Parkinson's disease, and Tourette's syndrome.

In some embodiments, the compound of the invention can also be used for the prevention or treatment of diabetes and/or diabetes-related disorders, particularly Type II diabetes, counteracting of insulin resistance, complications of diabetes, protection of pancreatic Langerhans islet beta-cells, antidiabetic therapies, therapy of syndrome X, diabetic neurosis, diabetic nephropathy, diabetic retinopathy, and for lifestyle-related diseases in an individual.

In some embodiments, the compound of the invention is used for the protection of pancreatic Langerhans islet beta-cells, therapy of syndrome X, or diabetic neurosis.

In some embodiments, the compound of the invention is used for the protection of pancreatic Langerhans islet beta-cells. In one embodiment, the compound is selected from Table 2. In one embodiment, the compound is CAS 26166-39-2 (Ascochlorin or Illicicolin D). In one embodiment, the compound is CAS 22562-67-0 (Illicicolin C). In one embodiment, the compound is CAS 22738-98-3 (Illicicolin F), In one embodiment, the compound is CAS 38965-84-3 (Chloronectrin).

In some embodiments, the compound of the invention can also be used for the prevention or treatment of disorders relating to lipid metabolism, particularly to those of the ligand of retinoid X receptor, ligand of nuclear receptor, PPAR-Agonist, PPAR-Antagonist, ligands activating nuclear receptor super family, and to the improvement of lipid metabolism, and antilipemic disease in an individual.

In some embodiments, the compound of the invention can also be used for the prevention or treatment of disorders related to vascular complications, particularly arteriosclerosis, hypertension, cerebrovascular diseases, hypotensive, hypertension, traumatic brain injury and cerebrovascular disorders in an individual.

In some embodiments, the compound of the invention can also be used for the prevention or treatment of cancer, particularly to control tumors, and digestive cancers in an individual.

In some embodiments, the compound of the invention can also be used for the prevention or treatment of inflammatory diseases, particularly rheumatoid arthritis, chronic inflammation, vascular chronic inflammation and the like in an individual.

In some embodiments, the compound of the invention can also be used as a stimulator of AMPK activity in an individual.

In some embodiments, the compound of the invention can also be used for the prevention or treatment of a series of other disorders, autoimmune diseases, anorectic, restenosis, myxedema, and cachexia in an individual.

The present invention also relates to the use of a compound of structural formula (Ia), (Ib), (Ic), I(d), (II), or (III) in the preparation of a product for the promotion of lactate secretion in an individual. In one embodiment, the compound is selected from Table 2. In one embodiment, the compound is CAS 26166-39-2 (Ascochlorin or Illicicolin D). In one embodiment, the compound is CAS 22562-67-0 (Illicicolin C). In one embodiment, the compound is CAS 22738-98-3 (Illicicolin F), In one embodiment, the compound is CAS 38965-84-3 (Chloronectrin).

The present invention also relates to the use of a compound of structural formula (Ia), (Ib), (Ic), I(d), (II), or (III) in the preparation of a product for the prevention or treatment of a neurological disorder in an individual. In one embodiment, the compound is selected from Table 2. In one embodiment, the compound is CAS 26166-39-2 (Ascochlorin or Illicicolin D). In one embodiment, the compound is CAS 22562-67-0 (Illicicolin C). In one embodiment, the compound is CAS 22738-98-3 (Illicicolin F), In one embodiment, the compound is CAS 38965-84-3 (Chloronectrin).

The present invention also relates to the use of a compound of formula (Ia), (Ib), (Ic), I(d), (II), or (III) in the preparation of a diet product. In one embodiment, the compound is selected from Table 2. In one embodiment, the compound is CAS 26166-39-2 (Ascochlorin or Illicicolin D). In one embodiment, the compound is CAS 22562-67-0 (Illicicolin C). In one embodiment, the compound is CAS 22738-98-3 (Illicicolin F), In one embodiment, the compound is CAS 38965-84-3 (Chloronectrin).

The present invention also relates to a method for the prevention or treatment of a neurological disorder comprising administering a compound of formula (Ia), (Ib), (Ic), I(d), (II), or (III) to an individual. In one embodiment, the compound is selected from Table 2. In one embodiment, the compound is CAS 26166-39-2 (Ascochlorin or Illicicolin D). In one embodiment, the compound is CAS 22562-67-0 (Illicicolin C). In one embodiment, the compound is CAS 22738-98-3 (Illicicolin F), In one embodiment, the compound is CAS 38965-84-3 (Chloronectrin).

EXAMPLES

The invention can be illustrated by way of the following examples, which should not be seen as limiting the scope of the invention.

Example 1

Lactate Release—Screening Assay

FIG. 1 shows the lactate screening strategy and the general workflow of the lactate release from the astrocytes drug discovery screen.

Human astrocytoma cell line CCF-STTG1 was cultured at 37° C. in a humidified atmosphere (5% CO2) in RPMI-1640 medium supplemented with 10% (v/v) heat-inactivated fetal calf serum, 50 µg/ml penicillin and 100 µg/ml streptomycin.

CCF-STTG1 were seeded in 384-well plates. Two days later, the cells were washed 3 times and incubated 30 min in Krebs-Ringer bicarbonate HEPES (KRBH) buffer containing (in mM): 140 NaCl, 3.6 KCl, 0.5 NaH2PO4, 0.5 MgSO4, 1.5 CaCl2, 10 HEPES, 5 NaHCO3 (pH7.4) supplemented with 2.5 mM glucose. Then, the cells were maintained in the buffer in the presence of tested compounds. Supernatants were collected after 2 hours and were assessed for lactate concentration. Lactate concentration in the supernatants were determined by fluorescent enzymatic assay. Samples were diluted in assay reagent containing (in mM or U/ml)): 100 sodium phosphate (pH7.5), 0.1 EDTA, 0.05 Amplex UltraRed, 0.1 Lactate oxidase, 1.5 Horseradish Peroxidase.

Fluorescence emission was measured at 600 nm after an excitation at 500 nm using Bioteck Synergie Neo multimode reader after 30 min at room temperature protected from direct light.

Example 2

Lactate Release—Counter Screen Assay

The compounds were also tested in absence of cells using the same fluorescent enzymatic assay described previously to assess their auto fluorescence or their interaction with the enzymatic assay. Fluorescence emission was measured at 600 nm after an excitation at 500 nm using Bioteck Synergie Neo multimode reader after 30 min at room temperature and protected from direct light. Fluorescence was then compared to control fluorescence obtained in basal and stimulated cells.

For the drug discovery counter screen, compounds diluted in KRBH were assessed for lactate release. The identified meroterpenoid compounds had no effect on the enzymatic assay in the absence of cells.

Example 3

Lactate Release—Orthogonal Assay

CCF-STTG1 were seeded in 384-well plates. Two days later, the cells were washed 3 times and incubated 30 min in Krebs-Ringer bicarbonate HEPES (KRBH) buffer containing (in mM): 140 NaCl, 3.6 KCl, 0.5 NaH2PO4, 0.5 MgSO4, 1.5 CaCl2, 10 HEPES, 5 NaHCO3 (pH7.4) supplemented with 2.5 mM glucose. The cells were maintained in the buffer in the presence of tested compounds. Supernatants were collected after 2 hours and assessed for lactate concentration. Lactate concentration in the supernatant was determined by a spectrophotometric enzymatic assay (lactate colorimetric assay kit II no. K627; BioVision, Milpitas, Calif. USA). In this kit, lactate is oxidized by lactate dehydrogenase to generate a product which interacts with a probe to produce a color ($\lambda$max=450 nm).

Absorbance was measure after 30 min at 450 nm using Bioteck Synergie Neo multimode reader. Background absorbance obtained in the absence of kit was subtracted from each value.

The stimulation of lactate secretion after treatment with meroterpenoid compounds was confirmed in an orthogonal assay based on another enzyme to measure lactate. The results of the lactate release measurement during the drug discovery screen for each compound and the results of lactate release measure with the orthogonal assay were correlated.

Dose response curves were established for compounds identified in the screen to stimulate lactate secretion. The EC50 values for the stimulation of lactate secretion were determined using primary human IPS cell derived astrocytes.

Differentiated human iPSCs (iCell astrocytes, and iCell cardiomyocytes) were obtained from Cellular Dynamics International (CDI, Madison, Wis., USA). iCell astrocytes were cultured in DMEM supplemented with 10% fetal calf serum and N2 complement. iCell cardiomyocytes were maintained in a medium supplied by CDI. Cell cultures were kept in a humidified atmosphere (5% CO2) at 37° C.

FIG. 2 shows lactate release. Dose response of compounds on lactate release from human iPSc derived into astrocyte fitted with a log (agonist) vs. response variable slope to extract efficacy (EC50). Mean±SEM in duplicate.

Example 4

Toxicity—ATP Content iCell Cardiomyocytes were seeded in 384-well plates. Eight days later cells were treated for 24 hours with compounds. Cell viability was determined by the quantification of intracellular ATP after cell lysis. ATP was used as an indicator of metabolically active cells. ATP was measured using a luminescent cell viability assay (CellTiter-Glo®; BioRad, Hercules, Calif., USA). Luminescence was measured after 20 min in a Bioteck Synergie Neo multimode reader.

Toxicity of the meroterpenoid compounds were evaluated in human IPS cell derived cardiomyocytes by measuring total ATP in cell lysates. Dose response experiments revealed that meroterpenoid compounds stimulated lactate secretion from astrocytes at concentrations several orders of magnitude below the concentration where they caused toxicity in cardiomyocytes.

FIG. 3 shows toxicity. Dose response of compounds on human iPSc derived into cardiomyocyte with evaluation of the ATP level using cell titer glow. Results were normalized between untreated cells (100%) and positive control (0%).

Example 5

Hit Evaluation

Table 1 and Table 2 show a list of compounds of interest

TABLE 1

| Chemical name | CAS Number | Primary screen % | Orthogonal assay % | Reconfirmation % |
|---|---|---|---|---|
| Ascochlorin | 26166-39-2 | | not tested | |
| Ilicicolin F | 22738-98-3 | 96 | 119 | 142 |
| Ilicicolin C | 22562-67-0 | 70 | 84 | 74 |
| Chloronectrin | 38965-84-3 | 104 | 68 | 97 |
| | 22581-11-9 | 68 | 61 | 50 |
| Antibiotic LL-Z1272ε | 22562-68-1 | 72 | 68 | 83 |
| Cylindrol B | 165187-16-6 | 100 | 67 | 61 |
| Lasalocid | 25999-31-9 | 88 | 53 | 73 |
| Amorfrutin | 80489-90-3 | 85 | 80 | 122 |
| 4-O-Demethyl amorfrutin B | 73436-04-1 | 82 | 68 | 77 |

TABLE 2

| | Astrocytes Lactate release | | Cardiomyocytes Toxicity | |
|---|---|---|---|---|
| CAS Number | EC50 [M] | logEC50 | IC50[M] | log IC50 |
| 26166-39-2 | 1.1E−08 | −7.9 | 1.2E−06 | −5.9 |
| 22738-98-3 | 2.7E−08 | −7.6 | 7.0E−06 | −5.2 |
| 22562-67-0 | 1.5E−07 | −6.8 | 7.1E−05 | −4.2 |
| 38965-84-3 | 5.0E−07 | −8.3 | 3.0E−05 | −4.5 |
| 22581-11-9 | 1.4E−08 | −7.9 | 3.2E−06 | −5.5 |
| 22562-68-1 | 2.6E−06 | −5.6 | 8.1E−05 | −4.1 |
| 165187-16-6 | 6.7E−06 | −5.2 | 3.1E−05 | −4.5 |
| 25999-31-9 | 4.4E−06 | −5.4 | 1.1E−05 | −4.9 |
| 80489-90-3 | 3.2E−06 | −5.5 | 4.7E−05 | −4.3 |
| 73436-04-1 | 1.0E−05 | −5.0 | t.b.d | t.b.d | t.b.d: to be determined

The toxicity expressed in log IC50 (ATP content after 24 hours compound treatment on human iPSc derived into cardiomyocyte) was compared against the lactate release in log EC50 (lactate secretion after 2 hours compound treatment in human iPSc derived into astrocytes). Meroterpenoid tested compounds showed a range of concentration where they are active on lactate secretion by astrocytes and not toxic on cardiomyocytes.

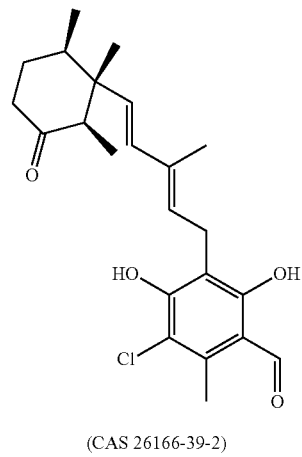

A (CAS 26166-39-2)

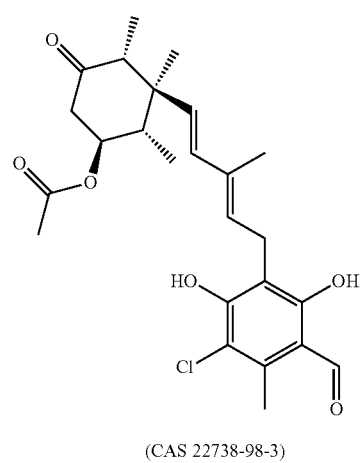

B (CAS 22738-98-3)

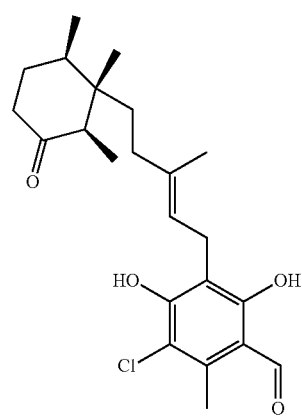

C (CAS 22562-67-0)

D
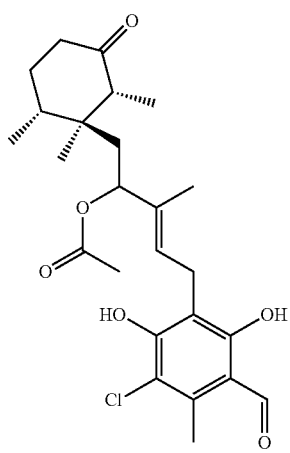
(CAS 38965-84-3)
E
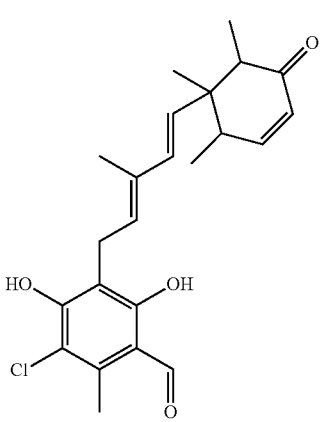
(CAS 22581-11-9)
F
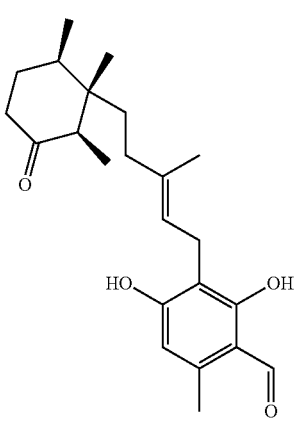
(CAS 22562-68-1)
G
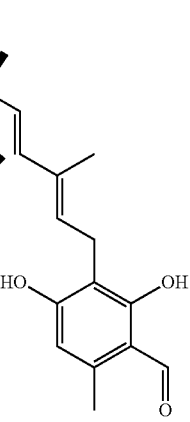
(CAS 165187-16-6)
H
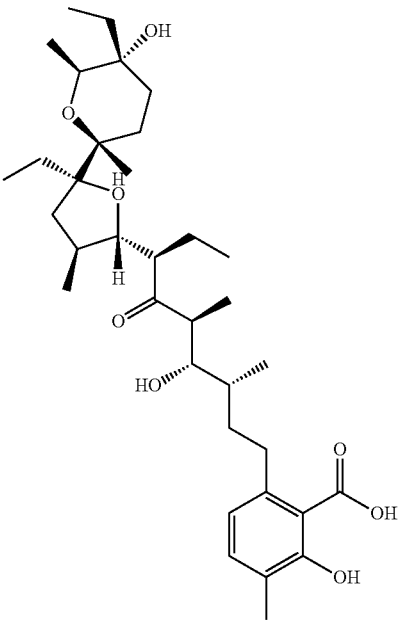
(CAS 25999-31-9)
I
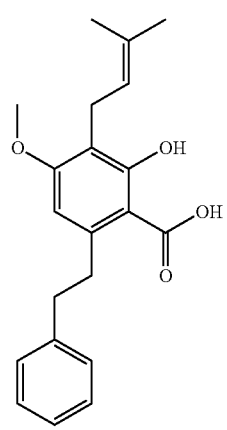
(CAS 80489-90-3)

Figure 1:
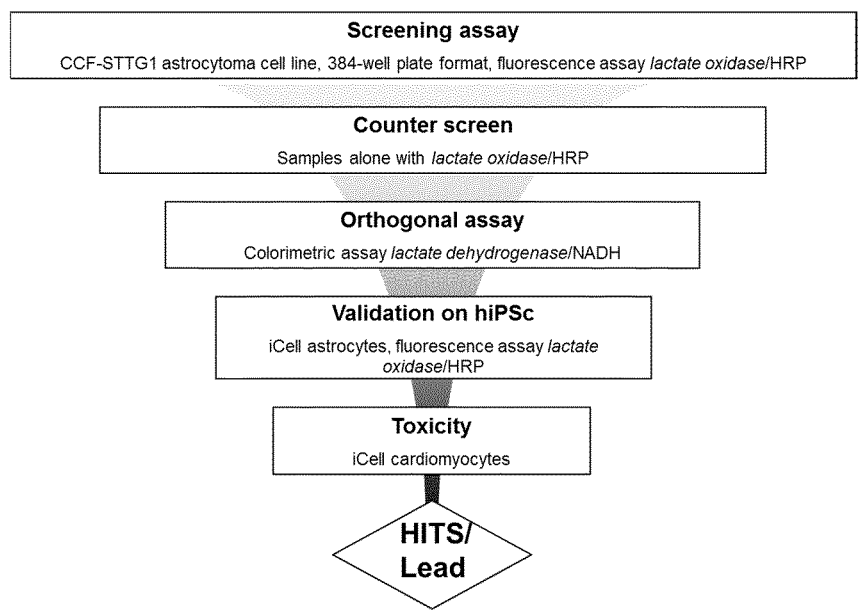
FIG. 1 shows the lactate screening strategy
Figure 2:
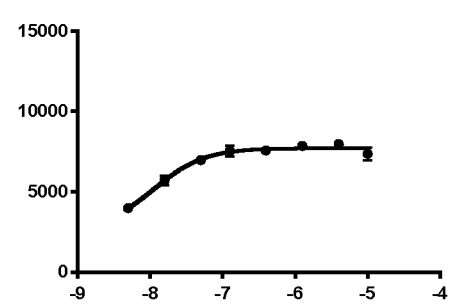
FIG. 2 shows lactate release. Y-axis: relative fluorescence unit, X-axis: logarithm concentration of the compound in molar. The structures of the compounds corresponding to graphs A-L are shown below.
Figure 2:
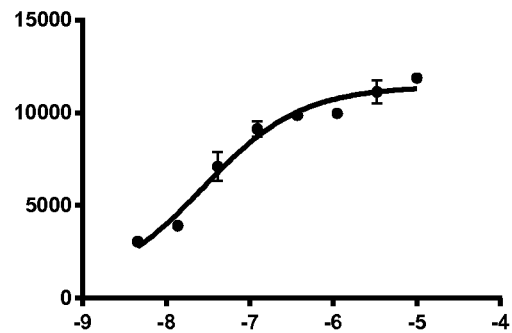
Figure 2:
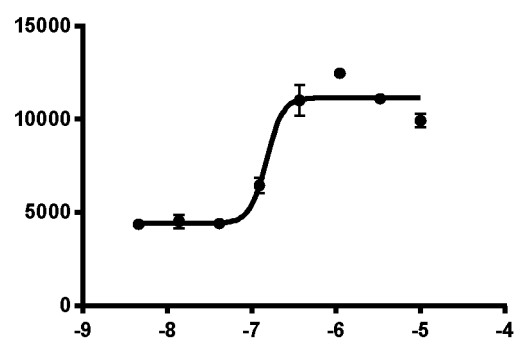
Figure 2:
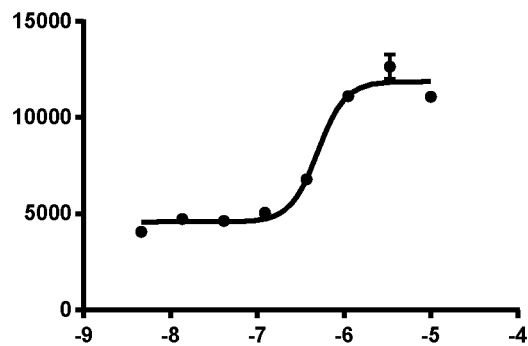
Figure 2:
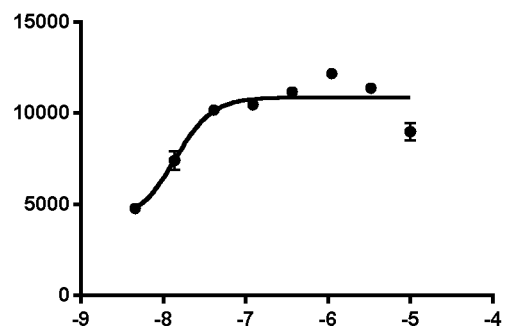
Figure 2:
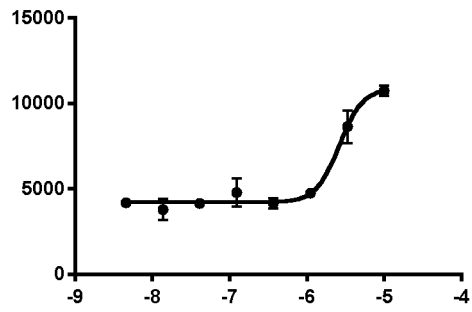
Figure 2:
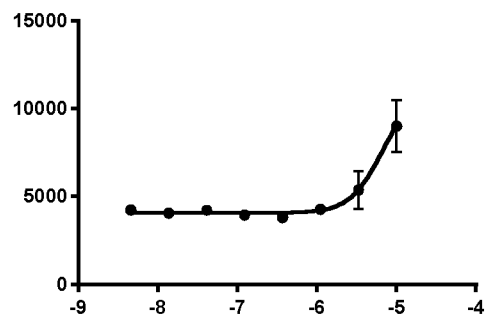
Figure 2:
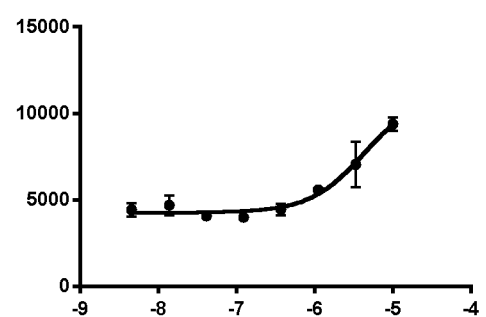
Figure 2:
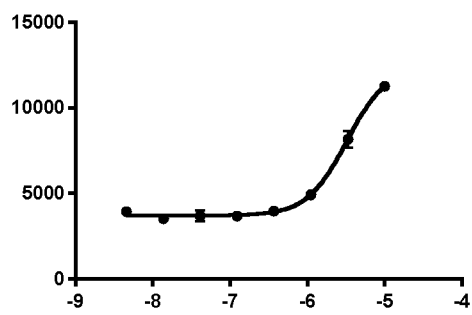
Figure 2:
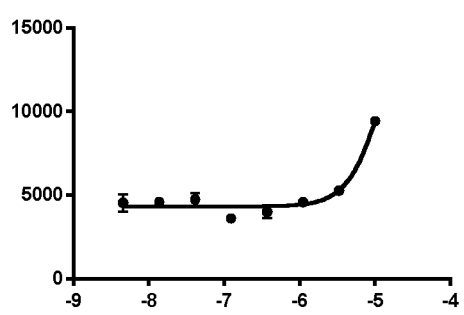
Figure 3:
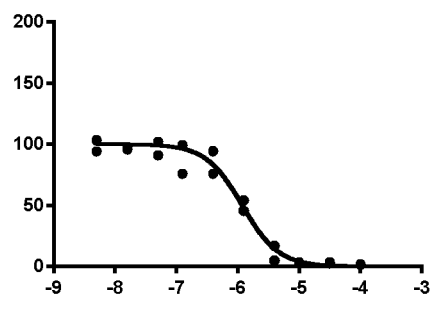
Figure 3:
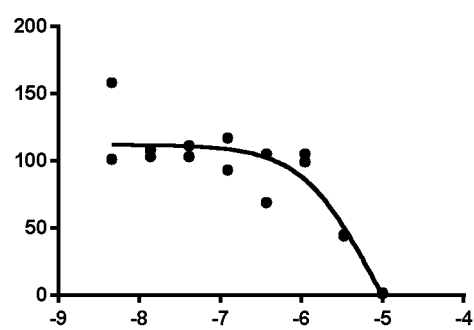
Figure 3:
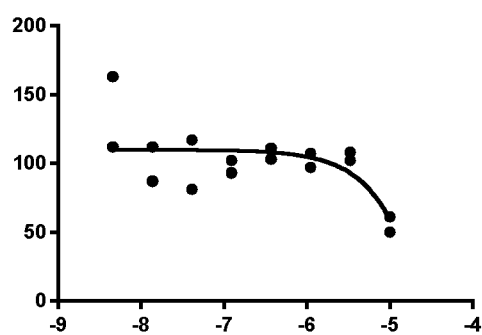
Figure 3:
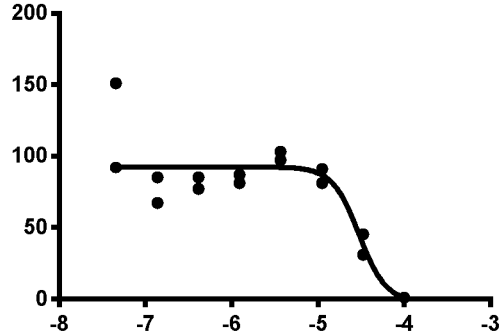
Figure 3:
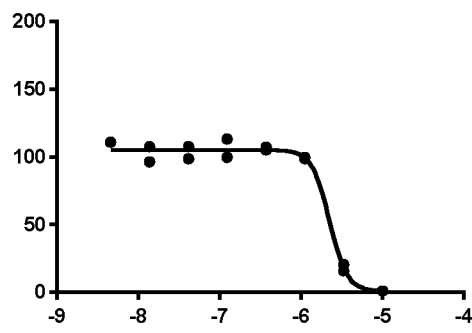
Figure 3:
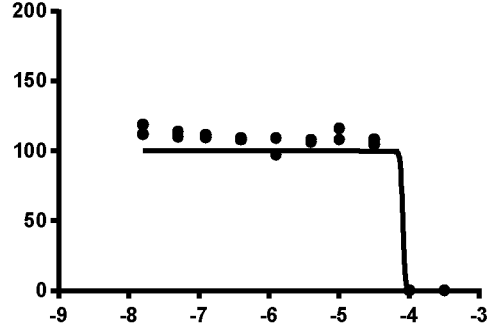
Figure 3:
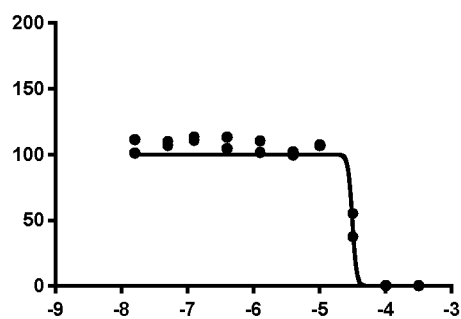
Figure 3:
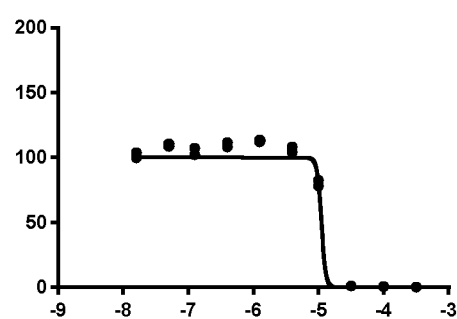
Figure 3:
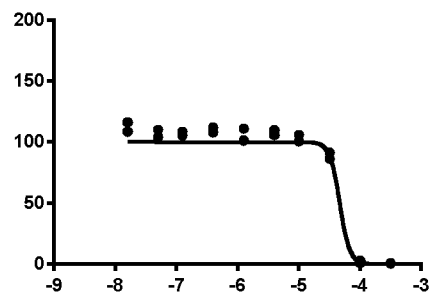

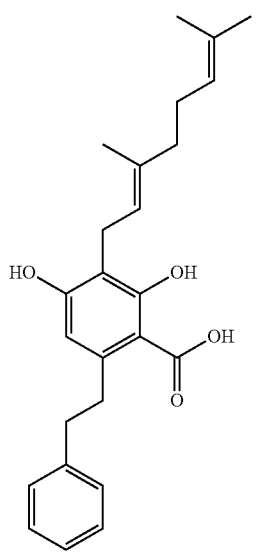
(CAS 73436-04-1)
FIG. 3 shows toxicity. Y-axis: relative fluorescence unit in percentage, X-axis: logarithm concentration of the compound in Molar. The structures of the compounds corresponding to graphs A-I are shown below.
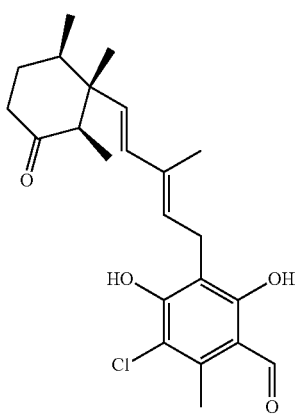
A
(CAS 26166-39-2)
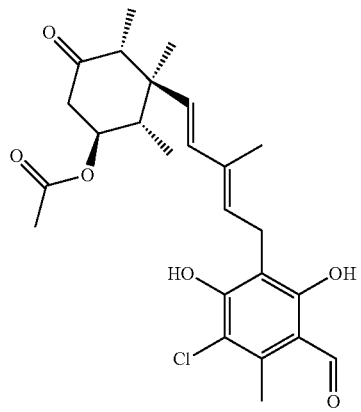
B
(CAS 22738-98-3)
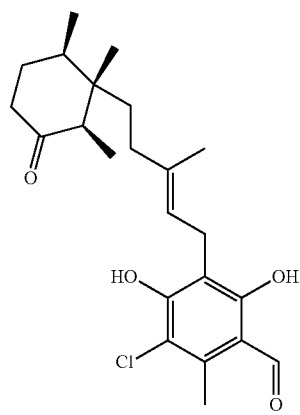
C
(CAS 22562-67-0)
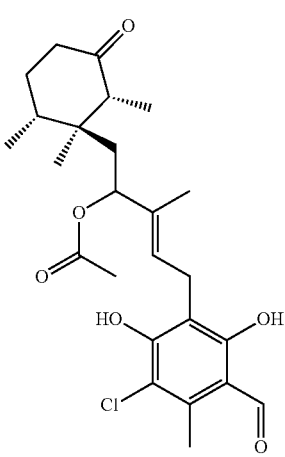
D
(CAS 38965-84-3)

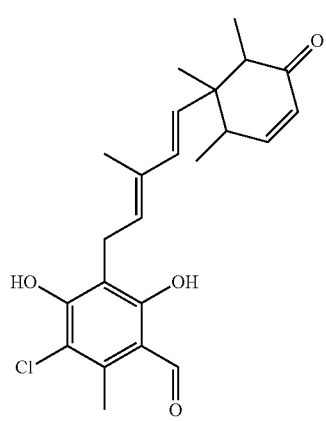

(CAS 22581-11-9)

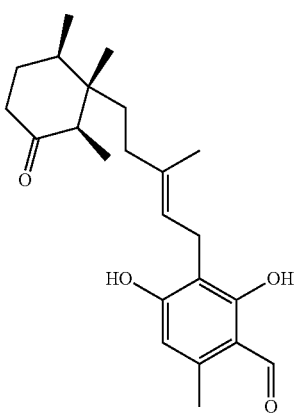

(CAS 22562-68-1)

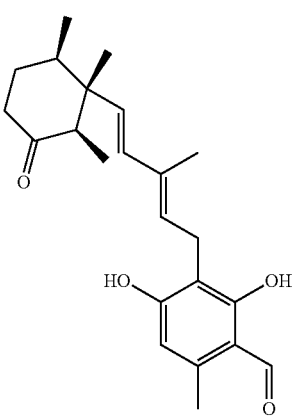

(CAS 165187-16-6)

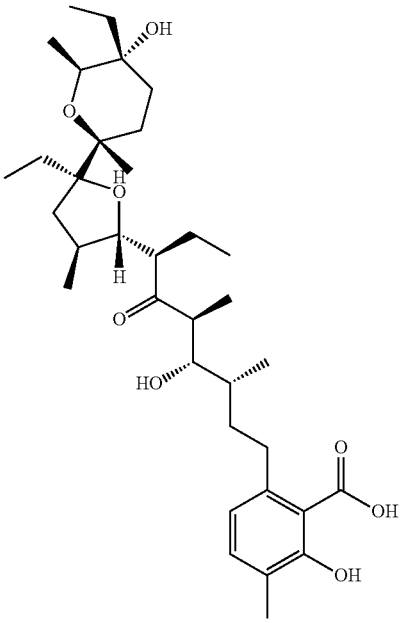

(CAS 25999-31-9)

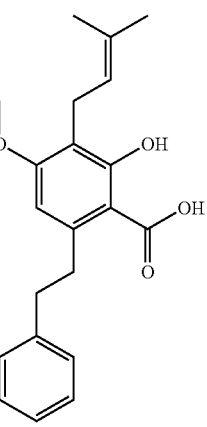

(CAS 80489-90-3)

The invention claimed is:

1. A method of increasing lactate secretion from brain cells of an elderly human, the method comprising administering a compound to the elderly human, the compound having the structural formula (Ib)

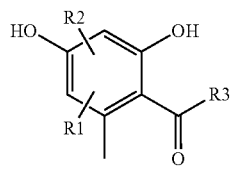

wherein R1=a halogen;
R2=cyclized isoprenoid chain with 5 to 19 carbon atoms, hydrogen, and optionally oxygen, and optionally with further esterification; and
R3=H or OH.

2. The method according to claim 1, wherein the compound has the structural formula

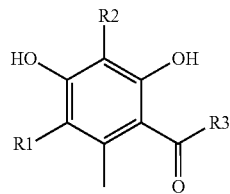

wherein R1=a halogen;
R2=cyclized isoprenoid chain with 5 to 19 carbon atoms, hydrogen, and optionally oxygen; and
R3=H or OH.

3. The method according to claim 1, wherein R1=Cl, and R3=H.

4. The method according to claim 1, wherein the compound is ascochlorin.

5. The method according to claim 1, where the compound is Illicicolin C (CAS 22562-67-0).

6. The method according to claim 1, where the compound is Illicicolin F (CAS 22738-98-3).

7. The method according to claim 1, wherein the lactate secretion from astrocytes is promoted.

8. The method according to claim 1, wherein the elderly human has a neurodegenerative disorder selected from the group consisting of Alzheimer's disease, Huntington's disease, Parkinson's disease, Tourette's syndrome, and combinations thereof.

9. The method according to claim 1, wherein the elderly human has cognitive impairment.

* * * * *